(12) United States Patent
Wang

(10) Patent No.: US 10,476,347 B2
(45) Date of Patent: Nov. 12, 2019

(54) IN-PROSTHESIS LINEAR DRIVE SYSTEM

(71) Applicant: HIWIN TECHNOLOGIES CORP., Taichung (TW)

(72) Inventor: Ren-Jeng Wang, Taichung (TW)

(73) Assignee: HIWIN TECHNOLOGIES CORP., Taichung (TW)

( * ) Notice: Subject to any disclaimer, the term of this patent is extended or adjusted under 35 U.S.C. 154(b) by 397 days.

(21) Appl. No.: 15/338,903

(22) Filed: Oct. 31, 2016

(65) Prior Publication Data
US 2018/0123424 A1   May 3, 2018

(51) Int. Cl.
  *H02K 7/06* (2006.01)
  *H02K 7/14* (2006.01)
  *H02K 7/116* (2006.01)
  *A61F 2/68* (2006.01)

(52) U.S. Cl.
  CPC .............. *H02K 7/06* (2013.01); *H02K 7/116* (2013.01); *H02K 7/14* (2013.01); *A61F 2/68* (2013.01)

(58) Field of Classification Search
  CPC ........ A61H 2201/123; A61F 2/68; A61F 2/70
  USPC .............................. 74/89.37, 89.33
  See application file for complete search history.

(56) References Cited

U.S. PATENT DOCUMENTS

| | | | |
|---|---|---|---|
| 2,417,434 A * | 3/1947 | Mead | F16H 25/2015 192/143 |
| 6,101,889 A * | 8/2000 | Laskey | F16H 25/2204 116/282 |
| 8,231,687 B2 | 7/2012 | Bedard et al. | |
| 8,287,477 B1 * | 10/2012 | Herr | A61B 5/1038 602/16 |
| 8,500,823 B2 | 8/2013 | Herr et al. | |
| 8,656,798 B2 * | 2/2014 | Kawahara | F16H 25/20 74/89.32 |
| 9,017,419 B1 | 4/2015 | Landry et al. | |
| 2004/0255705 A1 * | 12/2004 | Sullivan | B23Q 5/40 74/89.33 |
| 2010/0113980 A1 * | 5/2010 | Herr | A61F 2/60 600/587 |
| 2010/0312363 A1 * | 12/2010 | Herr | A61F 2/64 623/39 |
| 2011/0087339 A1 * | 4/2011 | Pusch | A61F 2/64 623/43 |

(Continued)

FOREIGN PATENT DOCUMENTS

CN   104382674 A   3/2015
JP   H11-325213 A   11/1999

(Continued)

*Primary Examiner* — Terence Boes
(74) *Attorney, Agent, or Firm* — Muncy, Geissler, Olds & Lowe, PC

(57) ABSTRACT

An in-prosthesis linear drive system includes a holder frame, a power drive mounted on the holder frame, a screw nut mounted on the holder frame and coupled to the power drive and rotatable on the axis thereof by the power drive, a screw rod limiter including a center sliding guide rail mounted on the holder frame and a center sliding block slidable along the center sliding guide rail, and a screw rod threaded into the screw nut and connected with the center sliding block of the screw rod limiter and movable along the axial direction of the screw nut upon rotation of the screw nut. Thus, using the screw nut to drive the screw rod achieves the effect of minimizing the occupation of the prosthesis internal space.

8 Claims, 4 Drawing Sheets

(56) References Cited

U.S. PATENT DOCUMENTS

| | | | |
|---|---|---|---|
| 2012/0259429 A1* | 10/2012 | Han | A61F 5/0127 623/24 |
| 2016/0158029 A1* | 6/2016 | Kuiken | A61F 2/60 623/24 |
| 2018/0085237 A1* | 3/2018 | Gao | A61F 2/66 |
| 2018/0116828 A1* | 5/2018 | Quinn | A61F 2/68 |
| 2018/0177664 A1* | 6/2018 | Choi | A61H 1/0259 |

FOREIGN PATENT DOCUMENTS

| | | |
|---|---|---|
| JP | 2002-543310 A | 12/2002 |
| JP | 2014-532391 A | 12/2014 |
| TW | M516509 U | 2/2016 |
| WO | 2016/130745 A1 | 8/2016 |

\* cited by examiner

IN-PROSTHESIS LINEAR DRIVE SYSTEM

BACKGROUND OF THE INVENTION

1. Field of the Invention

The present invention relates to linear driving technology and more particularly, to an in-prosthesis linear drive system that minimizes the occupation of the prosthesis internal space.

2. Description of the Related Art

In a linear drive system for prosthetic applications, for example, ball screw, a power drive, such as motor or speed reducer, is generally used for rotating a screw rod to cause forward or backward displacement of a screw nut along the screw rod, so that the screw nut can carry an attached structure forward or backward. The method of using a power drive to rotate a screw rod in moving a screw nut limits the installation of the power drive to the area around the two opposite ends of the screw rod, reducing the design flexibility of the installation of the linear drive system in the prosthesis. More particularly, when considering the stroke of the screw nut, the power drive must leave a space for enabling the screw nut to move unimpeded. Thus, the installation space in the prosthesis for the linear drive system cannot be effectively reduced, resulting in a large dimension of the prosthesis.

For example, in a ball screw, the screw rod is much longer than the screw nut. The application of the aforesaid method of using a power drive to drive the screw rod in moving the screw nut can be implemented in one of the following two ways. One way of the installation of the linear drive system is like the application of U.S. Pat. Nos. 8,231,687 and 8,287,477 where the motor is coupled with one end of the screw rod. Thus, the overall length of the linear drive system is greater than the length of the screw rod. In consequence, the internal space of the prosthesis must be greater than the length of the screw rod so that the linear drive system can be mounted therein. The other way of the installation of the linear drive system is like the application of U.S. Pat. No. 8,500,823 where the mounting location of the motor of the linear drive system must be beyond the space area around the screw rod so that the motor will not interfere with the movement of the screw nut along the screw rod. Thus, the width of the internal space of the prosthesis must be greater than the combined width of the screw rod and the screw nut, causing the internal space of the prosthesis unable to be effectively reduced.

SUMMARY OF THE INVENTION

The present invention has been accomplished under the circumstances in view. It is the main object of the present invention to provide an in-prosthesis linear drive system, which increases the prosthetic design flexibility and minimizes the occupation of the prosthesis internal space.

To achieve this object of the present invention, an in-prosthesis linear drive system comprises a holder frame, a power drive, a screw nut, a screw rod limiter and a screw rod. The power drive is mounted on the holder frame. The screw nut is rotatably mounted on the holder frame and coupled to the power drive. The screw rod limiter comprises a center sliding guide rail mounted on the holder frame and extended along the axial direction of the screw nut, and a center sliding block mounted on and slidable along the center sliding guide rail. The screw rod be threaded into the screw nut, having one end thereof connected to the center sliding block of the screw rod limiter such that the screw rod is axially movable forward or backward along the axial direction of the screw nut upon rotation of the screw nut.

Thus, the in-prosthesis linear drive system of the present invention uses the screw nut to drive the screw rod, causing the screw rod and the connected component to move axially back and forth along the axial direction of the screw rod. Thus, the screw nut can be selectively mounted at any location on the screw rod without limitation and, the power drive needs not to dodge the screw nut, minimizing the occupation of the prosthesis internal space.

Preferably, the in-prosthesis linear drive system further comprises a rail mount, a transmission sliding guide rail, a transmission sliding block and an adapter. The rail mount is mounted on the holder frame. The transmission sliding guide rail is mounted on the rail mount and disposed at one lateral side relative to the center sliding guide rail of the screw rod limiter. Further, the transmission sliding guide rail extends in a parallel manner relative to the extending direction of the center sliding rail of the screw rod limiter. The transmission sliding block is mounted on and slidable along the transmission sliding guide rail. The adapter is mounted on the transmission sliding block and connected to the center sliding block of the screw rod limiter for synchronous displacement with the screw rod. Thus, the in-prosthesis linear drive system can use the adapter for the connection of other components under different installation methods, provide a buffering force to the operation of the adapter by means of a buffer spring, and instantly detect the position of the adapter using a position sensor.

Other advantages and features of the present invention will be fully understood by reference to the following specification in conjunction with the accompanying drawings, in which like reference signs denote like components of structure.

DETAILED DESCRIPTION OF THE INVENTION

Figure 1:
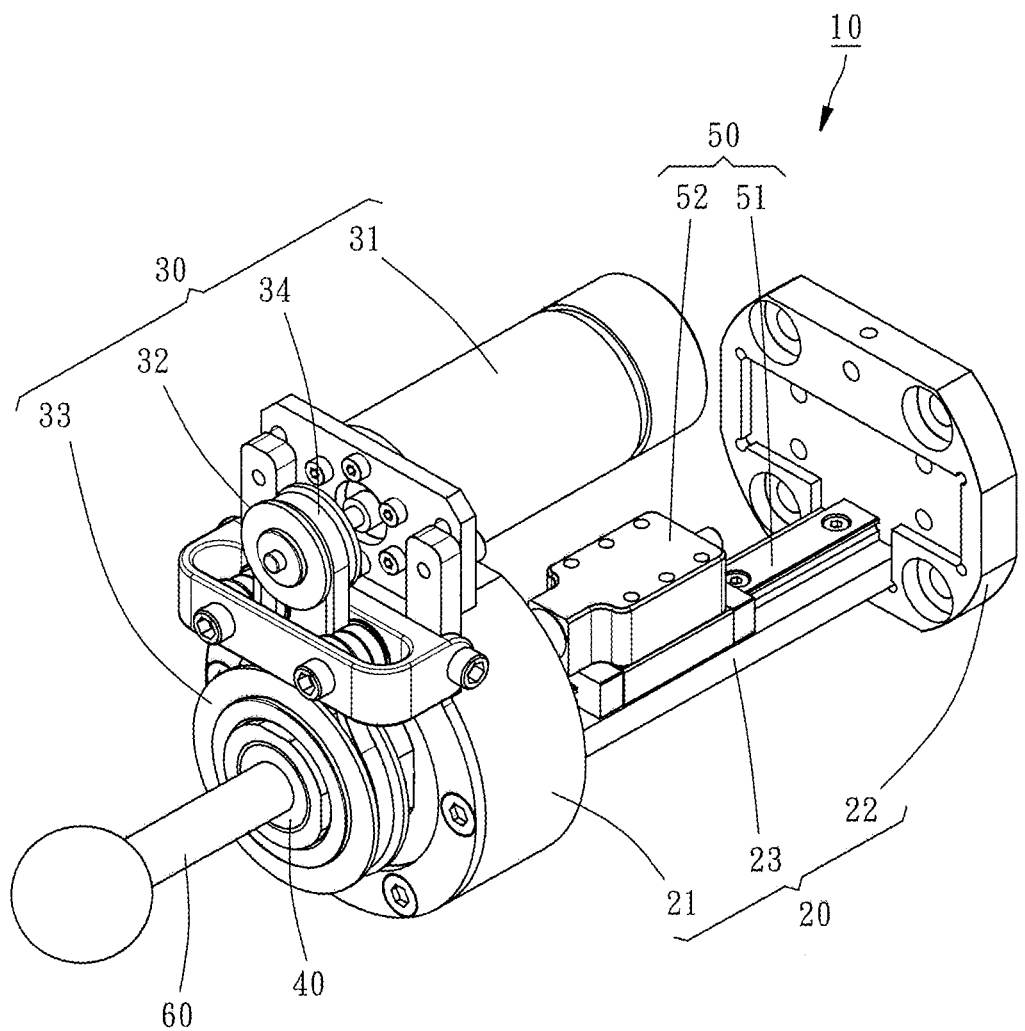
FIG. 1 is an oblique top elevational view of an in-prosthesis linear drive system in accordance with a first embodiment of the present invention.

Referring to FIG. 1, an in-prosthesis linear drive system 10 in accordance with a first embodiment of the present invention is shown. The in-prosthesis linear drive system 10 comprises a holder frame 20, a power drive 30, a screw nut 40, a screw rod limiter 50 and a screw rod 60.

The holder frame 20 comprises a first end block 21, a second end block 22, and a connection bar 23 connected between the first end block 21 and the second end block 22.

The power drive 30 comprises a motor 31, a first belt wheel 32, a second belt wheel 33 and a transmission belt 34. The motor 31 is mounted at the outer perimeter of the first end block 21 of the holder frame 20 for providing a driving force. The first belt wheel 32 is rotatably mounted at the outer perimeter of the first end block 21 of the holder frame 20 and connected to the motor 31. The second belt wheel 33 is rotatably mounted at an outer end surface of the first end block 21 of the holder frame 20. The transmission belt 34 is wound around the first belt wheel 32 and the second belt wheel 33. Thus, when the motor 31 is started up, the first belt wheel 32 is rotated by the motor 31, causing the transmission belt 34 to rotate the second belt wheel 33.

The screw nut 40 is mounted in the first end block 21 of the holder frame 20 and coupled to a center hole (not shown) of the second belt wheel 33 of the power drive 30. Thus, the screw nut 40 is drivable by the second belt wheel 33 of the power drive 30 to rotate on its own axis.

The screw rod limiter 50 comprises a center sliding guide rail 51 fixedly mounted on the connection bar 23 of the holder frame 20 and extended in parallel to the axial direction of the screw nut 40, and a center sliding block 52 slidably mounted on the center sliding guide rail 51.

The screw rod 60 is threaded into the screw nut 40, having one end thereof adapted for connection to a driven component part (not shown) and an opposite end thereof inserted through the first end block 21 of the holder frame 20 and connected with the center sliding block 52 of the screw rod limiter 50. Thus, the screw rod 60 is constrained by the screw rod limiter 50 to reciprocate axially along the axial direction of the screw nut 40 when the screw nut 40 is rotated.

It can be seen from the above description that the in-prosthesis linear drive system 10 has the advantages as follows:

1. In the in-prosthesis linear drive system 10 of the present invention, the power drive 30 is adapted for driving the screw nut 40 to move the screw rod 60, causing the screw rod 60 to carry the connected driven component part axially forwards and backwards along the axial direction of the screw nut 40, and thus, the screw nut 40 can be selectively mounted at any location on the screw rod 60 without limitation. Further, the power drive 30 needs not to dodge the screw nut 40. Through the arrangement that the power drive 30 and the screw nut 40 are displaced from each other, the accommodation space of the prosthetic limb can be smaller than the combined width of the power drive 30 and the screw nut 40, increasing the prosthetic design flexibility.

2. In the prior art designs, the driven component part must be installed together with the screw nut, causing the occupation of installation space unable to be effectively reduced. In the present invention, the driven component part is mounted at the screw rod 60 but not at the screw nut 40, and thus, the installation of the driven component part does not need to match with the position of the screw nut 40, enabling the overall dimension of the linear drive system to be minimized so as to significantly reduce space occupation.

Figure 2:
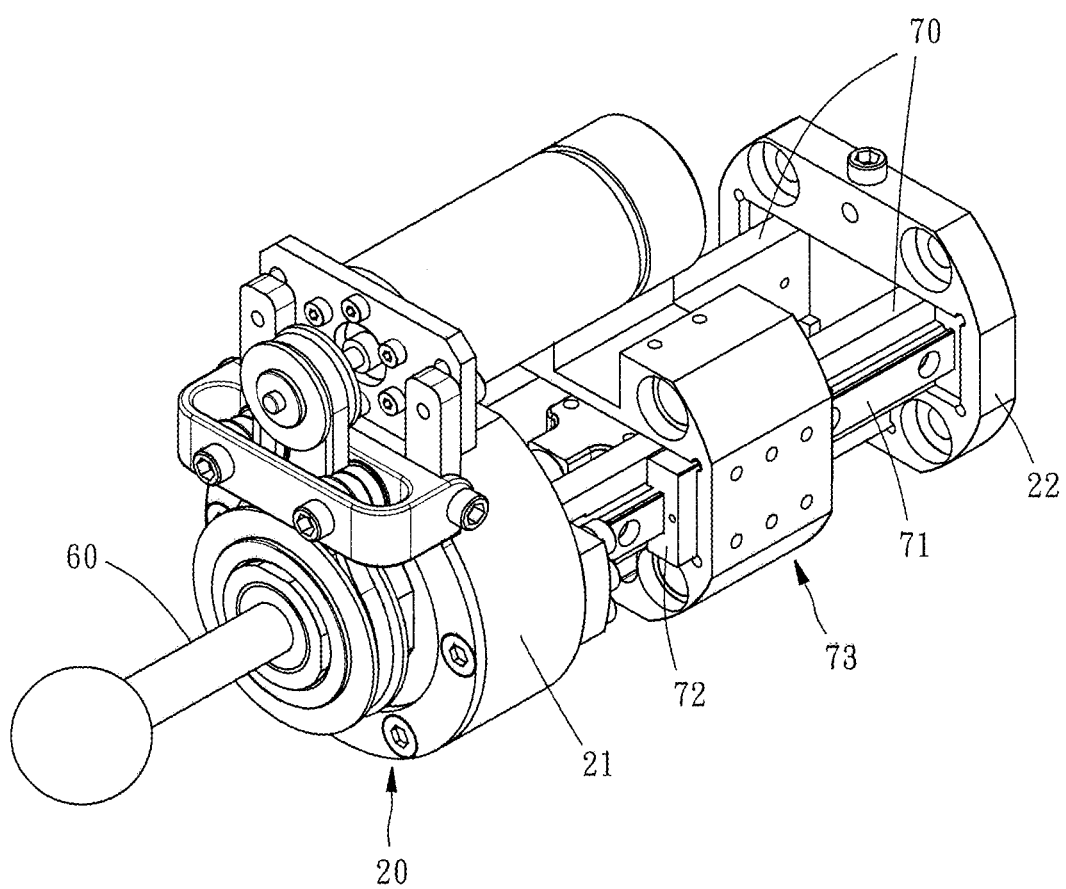
FIG. 2 is an oblique top elevational view of an in-prosthesis linear drive system in accordance with a second embodiment of the present invention.
Figure 4:
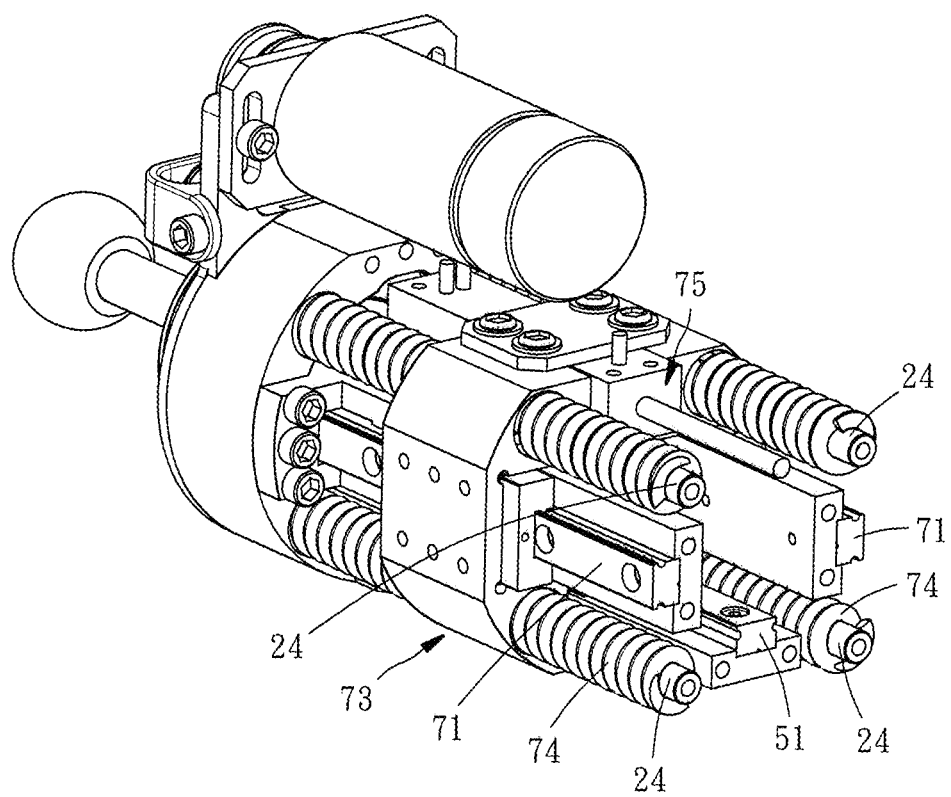
FIG. 4 corresponds to FIG. 3 when viewed from another angle.

Referring to FIGS. 2 and 4, an in-prosthesis linear drive system in accordance with a second embodiment of the present invention is shown. This second embodiment is substantially similar to the aforesaid first embodiment with the exception that this second embodiment further comprises two rail mounts 70, two transmission sliding guide rails 71, two transmission sliding blocks 72, and an adapter 73.

The rail mounts 70 have respective two opposite ends thereof respectively connected to the first end block 21 and the second end block 22 of the holder frame 20.

The transmission sliding guide rails 71 are respectively affixed to respective outer sides of the rail mounts 70 and respectively disposed at two opposite lateral sides relative to the center sliding guide rail 51 of the screw rod limiter 50.

Further, the transmission sliding guide rails 71 are equally spaced around the centered screw rod 60 and respectively arranged at right angles relative to the center sliding guide rail 51 of the screw rod limiter 50. Further, the transmission sliding guide rails 71 extend in a parallel manner relative to the extending direction of the center sliding guide rail 51 of the screw rod limiter 50.

The transmission sliding blocks 72 are respectively mounted on and slidable along the transmission sliding guide rails 71 between the first end block 21 and the second end block 22 of the holder frame 20.

The adapter 73 is mounted on the transmission sliding blocks 72 and connected to the center sliding block 52 of the screw rod limiter 50. By means of the center sliding block 52, the adapter 73 is synchronously movable with the screw rod 60.

It can be seen from the above description that the in-prosthesis linear drive system 10 uses the adapter 73 to carry a driven component. When compared to the aforesaid first embodiment, this second embodiment enhances the operation stability and allows change of application according to actual requirements.

Figure 3:
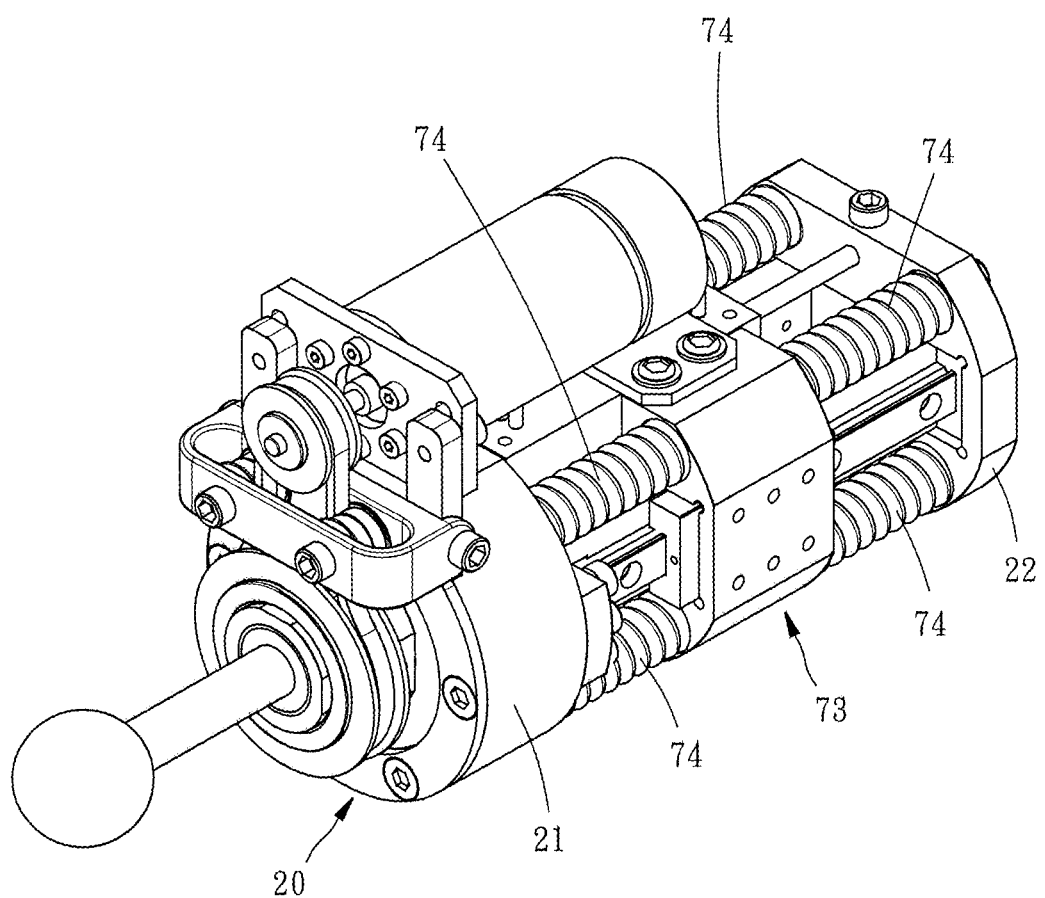
FIG. 3 is an oblique top elevational view of an in-prosthesis linear drive system in accordance with a third embodiment of the present invention.

In a third embodiment of the present invention, as illustrated in FIG. 3 and FIG. 4, the holder frame 20 further comprises four spring supporting rod members 24 respectively inserted through four corners of the adapter 72 and connected between the first end block 21 and the second end block 22 of the holder frame 20, and a plurality of buffer springs 74 respectively sleeved onto the spring supporting rod members 24 and respectively stopped between the first end block 21 and the adapter 72 and between the second end block 22 and the adapter 72. Thus, during displacement of the adapter 73, the buffer springs 74 provide a buffering effect, enhancing the operation stability of the adapter 73. Further, the adapter 73 can be worked with a position sensor 75. During displacement of the adapter 73, the position sensor 75 instantly detects the position of the adapter 73 so that an appropriate adjustment can be done according to the result of the detection.

In conclusion, the invention uses the screw nut 40 to move the screw rod 60, not only can increase design flexibility and reduce space occupation, but also can enhance the ability to resist against external forces. Further, with the use of the adapter 73, the in-prosthesis linear drive system of the present invention can be operated in different ways, achieving the objects of the present invention.

What is claimed is:

1. An in-prosthesis linear drive system, comprising:
a holder frame;
a power drive mounted on said holder frame;
a screw nut rotatably mounted on said holder frame and coupled to said power drive and rotatable on the axis thereof by said power drive;
a screw rod limiter comprising a center sliding guide rail mounted on said holder frame and extended along the axial direction of said screw nut, and a center sliding block mounted on and slidable along said center sliding guide rail; and
a screw rod threaded into said screw nut, said screw rod having a terminal end parallel to the axial direction of said screw nut, said terminal end being provided with a terminal end portion connected to said center sliding block of said screw rod limiter such that said screw rod is axially movable forward or backward along the axial direction of said screw nut upon rotation of said screw nut.

2. The in-prosthesis linear drive system as claimed in claim 1, wherein said holder frame comprises a first end block, a second end block, and a connection bar connected between said first end block and said second end block; said power drive is mounted on the outer perimeter of said first end block; said center sliding guide rail is mounted on said connection bar.

3. The in-prosthesis linear drive system as claimed in claim 1, wherein said power drive comprises a motor mounted on the outer perimeter of said first end block of said holder frame, a first belt wheel rotatably mounted on the outer perimeter of said first end block of said holder frame and coupled to and rotatable by said motor, a second belt wheel rotatably mounted on an outer end surface of said first end block of said holder frame and coupled with said screw nut, and a transmission belt wound around said first belt wheel and said second belt wheel.

4. The in-prosthesis linear drive system as claimed in claim 1, further comprising a rail mount mounted on said holder frame, a transmission sliding guide rail mounted on said rail mount and disposed at one lateral side relative to said center sliding guide rail of said screw rod limiter and extending in a parallel manner relative to the extending direction of said center sliding guide rail of said screw rod limiter, a transmission sliding block mounted on and slidable along said transmission sliding guide rail, and an adapter mounted on said transmission sliding block and connected to said center sliding block of said screw rod limiter for synchronous displacement with said screw rod.

5. The in-prosthesis linear drive system as claimed in claim 4, wherein said center sliding guide rail and said transmission sliding guide rail are arranged at right angles relative to the centered said screw rod.

6. The in-prosthesis linear drive system as claimed in claim 4, further comprising at least one buffer spring supported between said holder frame and said adapter.

7. The in-prosthesis linear drive system as claimed in claim 6, wherein said holder frame comprises a first end block, a second end block and a connection bar connected between said first end block and said second end block; said power drive is mounted at an outer perimeter of said first end block; said screw nut is mounted in said first end block; said center sliding guide rail is mounted on said connection bar; said rail mount has two opposite ends thereof respectively connected to said first end block and said second end block; said adapter is disposed between said first end block and said second end block; the number of said at least one buffer spring is at least 2 with at least one said buffer spring supported between said first end block of said holder frame and said adapter and at least another said buffer spring supported between said second end block of said holder frame and said adapter.

8. The in-prosthesis linear drive system as claimed in claim 4, further comprising a position sensor mounted on said adapter and adapted for detecting the position of said adapter.

* * * * *